United States Patent
Herold et al.

(10) Patent No.: US 7,615,664 B2
(45) Date of Patent: Nov. 10, 2009

(54) PHENYLOCTANAMIDES

(75) Inventors: Peter Herold, Basel (CH); Stefan Stutz, Basel (CH); Robert Mah, Muttenz (CH); Vincenzo Tschinke, Binningen (CH); Christiane Marti, Rheinfelden (CH)

(73) Assignee: Speedel Experimenta AG, Allschwil (CH)

( * ) Notice: Subject to any disclaimer, the term of this patent is extended or adjusted under 35 U.S.C. 154(b) by 245 days.

(21) Appl. No.: 11/792,673

(22) PCT Filed: Dec. 9, 2005

(86) PCT No.: PCT/EP2005/056622

§ 371 (c)(1),
(2), (4) Date: Jun. 8, 2007

(87) PCT Pub. No.: WO2006/061426

PCT Pub. Date: Jun. 15, 2006

(65) Prior Publication Data

US 2008/0153902 A1    Jun. 26, 2008

(30) Foreign Application Priority Data

Dec. 10, 2004  (CH) .................................... 2048/04

(51) Int. Cl.
C07C 233/05  (2006.01)
A61K 31/65  (2006.01)

(52) U.S. Cl. ...................... 564/165; 549/378; 514/452; 514/620

(58) Field of Classification Search ................. 564/165; 549/378; 514/452, 620
See application file for complete search history.

(56) References Cited

U.S. PATENT DOCUMENTS 4,396,627 A * 8/1983 Ainsworth et al. .......... 514/533

| 5,559,111 | A | 9/1996 | Göschke et al. |
| 7,241,810 | B2 * | 7/2007 | Brown et al. ................. 514/616 |
| 7,482,487 | B2 * | 1/2009 | Brown et al. ................. 564/165 |
| 2003/0114389 | A1 | 6/2003 | Webb |

FOREIGN PATENT DOCUMENTS

| EP | 0 678 503 | 10/1995 |
| WO | 2005/090305 | 9/2005 |

OTHER PUBLICATIONS

Jeanette M. Wood et al., "Structure-based design of aliskiren, a novel orally effective renin inhibitor", Biochemical and Biophysical Research Communications, Academic Press Inc., vol. 308, No. 4, pp. 698-705, XP004447169, ISSN: 0006-291X, Sep. 5, 2003.

Richard Göschke et al., "Design and synthesis of novel, 2,7-Dialkyl Substituted 5(S)-Amino-4(S)-Hydroxy-8-Phenyl-Octanecarboxamides as In Vitro Potent Peptidomimetic Inhibitors of Human Renin", Bioorganic & Medicinal Chemistry Letters, vol. 7, No. 21, pp. 2735-2740, XP004136522, ISSN: 0960-894X, Nov. 4, 1997.

\* cited by examiner

*Primary Examiner*—Shailendra Kumar
(74) *Attorney, Agent, or Firm*—Wenderoth, Lind & Ponack, L.L.P.

(57) ABSTRACT

Compounds of the general formula (I) in which the substituents R, $R_1$, $R_2$, $R_3$, $R_4$, $R_5$ and $R_6$ are each as defined in claim 1 have renin-inhibiting properties and can be used as medicaments.

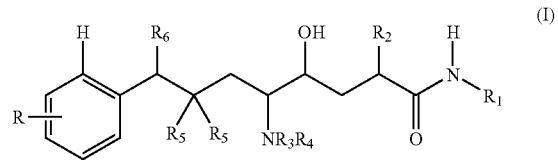

9 Claims, No Drawings

PHENYLOCTANAMIDES

This application is a 371 of PCT/EP2005/056622, filed Dec. 9, 2005.

The present invention relates to novel alkanamides, to processes for their preparation and to the use of the compounds as medicaments, in particular as renin inhibitors.

Alkanamides for use as medicaments are known, for example, from EP 0678503. With regard to renin inhibition in particular, however, there is still a need for highly potent active ingredients. In this context, the improvement of the pharmacokinetic properties is at the forefront. These properties directed towards better bioavailability are, for example, absorption, metabolic stability, solubility or lipophilicity.

The invention therefore provides compounds of the general formula

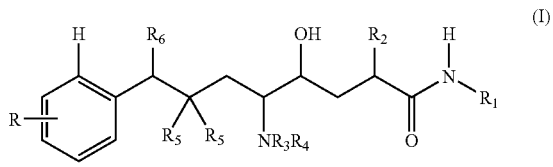

in which $R_1$ is aryl which is optionally substituted;

$R_2$ is $C_1$-$C_8$-alkyl, $C_2$-$C_8$-alkenyl or $C_3$-$C_8$-cycloalkyl or is phenyl- or naphthyl-$C_1$-$C_4$-alkyl, each of which is unsubstituted or mono-, di- or trisubstituted by $C_1$-$C_4$-alkyl, $C_1$-$C_4$-alkoxy, hydroxyl, $C_1$-$C_4$-alkylamino, N,N-di-$C_1$-$C_4$-alkylamino, halogen and/or trifluoromethyl;

$R_3$ is hydrogen, $C_1$-$C_4$-alkyl or $C_1$-$C_8$-alkanoyl;

$R_4$ is hydrogen, $C_1$-$C_4$-alkyl or $C_1$-$C_8$-alkanoyl;

$R_5$ are each independently hydrogen, $C_1$-$C_8$-alkyl or, together with the carbon atom to which they are bonded, a $C_3$-$C_8$-cycloalkylidene radical;

$R_6$ is hydrogen or hydroxyl;

R are each independently 1-4 radicals selected from:

hydrogen, halogen, $C_1$-$C_8$-alkyl, 3- to 8-membered cycloalkyl, polyhalo-$C_1$-$C_4$-alkyl, polyhalo-$C_1$-$C_4$-alkoxy, $C_1$-$C_4$-alkoxy-$C_1$-$C_4$-alkyl, $C_1$-$C_4$-alkoxy-$C_1$-$C_4$-alkoxy-$C_1$-$C_4$-alkyl, 3- to 8-membered cycloalkoxy-$C_1$-$C_4$-alkyl, hydroxyl, $C_1$-$C_8$-alkanoyloxy-$C_1$-$C_4$-alkyl, hydroxy-$C_2$-$C_8$-alkyl, $C_1$-$C_4$-alkylthio-$C_1$-$C_4$-alkyl, $C_1$-$C_8$-alkanesulphonyl-$C_1$-$C_4$-alkyl, thiazolylthio-$C_1$-$C_4$-alkyl, thiazolinylthio-$C_1$-$C_4$-alkyl, imidazolylthio-$C_1$-$C_4$-alkyl, optionally N-oxidized pyridylthio-$C_1$-$C_4$-alkyl, pyrimidinylthio-$C_1$-$C_4$-alkyl, optionally partially hydrogenated pyridyl- or N-oxidopyridyl-$C_1$-$C_4$-alkyl, $C_1$-$C_4$-alkanesulphonylamino-$C_1$-$C_4$-alkyl, trifluoro-$C_1$-$C_8$-alkanesulphonylamino-$C_1$-$C_4$-alkyl, pyrrolidino-$C_1$-$C_4$-alkyl, piperidino-$C_1$-$C_4$-alkyl, piperazino-$C_1$-$C_4$-alkyl, N'-$C_1$-$C_4$-alkylpiperazino-$C_1$-$C_4$-alkyl, N'-$C_2$-$C_8$-alkanoylpiperazino-$C_1$-$C_4$-alkyl, morpholino-$C_1$-$C_4$-alkyl, thiomorpholino-$C_1$-$C_4$-alkyl, S-oxothiomorpholino-$C_1$-$C_4$-alkyl, S,S-dioxothiomorpholino-$C_1$-$C_4$-alkyl, cyano-$C_1$-$C_4$-alkyl, carboxy-$C_1$-$C_4$-alkyl, $C_1$-$C_4$-alkoxycarbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, optionally by $C_1$-$C_4$-alkyl, $C_1$-$C_4$-alkoxy, hydroxyl, $C_1$-$C_4$-alkylamino, di-$C_1$-$C_4$-alkylamino, halogen and/or trifluoromethyl mono-, di- or trisubstituted phenyl, optionally by $C_1$-$C_4$-alkyl, $C_1$-$C_4$-alkoxy, hydroxyl, $C_1$-$C_4$-alkylamino, di-$C_1$-$C_4$-alkylamino, halogen and/or trifluoromethyl mono-, di- or trisubstituted naphthyl, hydroxy-$C_2$-$C_8$-alkoxy, halo-$C_2$-$C_8$-(hydroxy)alkoxy, $C_1$-$C_8$-alkanesulphonyl-$C_1$-$C_4$-(hydroxy)alkoxy, amino-$C_1$-$C_4$-alkyl, $C_1$-$C_4$-alkylamino-$C_1$-$C_4$-alkyl, N,N-di-$C_1$-$C_4$-alkylamino-$C_1$-$C_4$-alkyl, N—$C_1$-$C_4$-alkanoylamino-$C_1$-$C_4$-alkyl, $C_1$-$C_8$-alkoxycarbonylamino-$C_2$-$C_8$-alkyl, amino-$C_1$-$C_4$-alkoxy, $C_1$-$C_4$-alkylamino-$C_1$-$C_4$-alkoxy, N,N-di-$C_1$-$C_4$-alkylamino-$C_1$-$C_4$-alkoxy, $C_1$-$C_8$-alkanoylamino-$C_1$-$C_4$-alkoxy, $C_1$-$C_8$-alkoxycarbonylamino-$C_2$-$C_8$-alkoxy, $C_1$-$C_8$-alkanoyl-$C_2$-$C_4$-alkoxy which bears the alkanoyl group in higher than the α-position, $C_1$-$C_8$-alkoxy, 3- to 8-membered cycloalkoxy, $C_2$-$C_8$-alkenyloxy, 3- to 8-membered cycloalkoxy-$C_1$-$C_4$-alkoxy, $C_1$-$C_4$-alkoxy-$C_1$-$C_4$-alkoxy, $C_1$-$C_4$-alkoxy-$C_2$-$C_4$-alkenyl, $C_2$-$C_8$-alkenyloxy-$C_1$-$C_4$-alkoxy, $C_1$-$C_4$-alkoxy-$C_2$-$C_4$-alkenyloxy, $C_2$-$C_8$-alkenyloxy-$C_1$-$C_4$-alkyl, $C_1$-$C_4$-alkylthio-$C_1$-$C_4$-alkoxy, $C_1$-$C_8$-alkanesulphonyl-$C_1$-$C_4$-alkoxy, $C_1$-$C_4$-alkylthio-$C_1$-$C_4$-(hydroxy)alkoxy, optionally by $C_1$-$C_4$-alkyl, $C_1$-$C_4$-alkoxy, hydroxyl, $C_1$-$C_4$-alkylamino, di-$C_1$-$C_4$-alkylamino, halogen and/or trifluoromethyl mono-, di- or trisubstituted phenyl-$C_1$-$C_4$-alkoxy, optionally by $C_1$-$C_4$-alkyl, $C_1$-$C_4$-alkoxy, hydroxyl, $C_1$-$C_4$-alkylamino, di-$C_1$-$C_4$-alkylamino, halogen and/or trifluoromethyl mono-, di- or trisubstituted naphthyl-$C_1$-$C_4$-alkoxy, each of which is unsubstituted or mono-, di- or trisubstituted by $C_1$-$C_4$-alkyl, $C_1$-$C_4$-alkoxy, hydroxyl, $C_1$-$C_4$-alkylamino, di-$C_1$-$C_4$-alkylamino, halogen and/or trifluoromethyl, polyhalo-$C_1$-$C_4$-alkoxy, optionally partially hydrogenated pyridyl- or N-oxidopyridyl-$C_1$-$C_4$-alkoxy, thiazolyl-$C_1$-$C_4$-alkoxy, optionally N-oxidized morpholino-$C_1$-$C_4$-alkoxy, thiazolylthio-$C_1$-$C_4$-alkoxy, thiazolinylthio-$C_1$-$C_4$-alkoxy, imidazolylthio-$C_1$-$C_4$-alkoxy, optionally N-oxidized pyridylthio-$C_1$-$C_4$-alkoxy, pyrimidinylthio-$C_1$-$C_4$-alkoxy, $C_1$-$C_8$-alkanesulphonylamino-$C_1$-$C_4$-alkoxy, trifluoro-$C_1$-$C_8$-alkanesulphonyl-$C_1$-$C_4$-alkoxy, pyrrolidino-$C_1$-$C_4$-alkoxy, piperidino-$C_1$-$C_4$-alkoxy, cyano-$C_1$-$C_4$-alkoxy, carboxy-$C_1$-$C_4$-alkoxy, $C_1$-$C_4$-alkoxycarbonyl-$C_1$-$C_4$-alkoxy, carbamoyl-$C_1$-$C_4$-alkoxy, N-$C_1$-$C_8$-alkylcarbamoyl-$C_1$-$C_4$-alkoxy, N-mono- or N,N-di-$C_1$-$C_4$-alkylcarbamoyl-$C_1$-$C_4$-alkoxy, carboxy-$C_1$-$C_4$-alkyl, $C_1$-$C_4$-alkoxycarbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, carboxy-$C_1$-$C_4$-alkoxy, $C_1$-$C_4$-alkoxycarbonyl-$C_1$-$C_4$-alkoxy, carbamoyl-$C_1$-$C_8$-alkoxy, $C_1$-$C_4$-alkylamino or N,N-di-$C_1$-$C_4$-alkylamino, and salts, especially pharmaceutically usable salts thereof.

Aryl contains generally 6-14, preferably 6-10, carbon atoms and is, for example, phenyl, indenyl, e.g. 2- or 4-indenyl, or naphthyl, e.g. 1- or 2-naphthyl. Preference is given to aryl having 6-10 carbon atoms, in particular phenyl or 1- or 2-naphthyl. The radicals mentioned may be unsubstituted or, for example, be mono- or polysubstituted, for example mono- or disubstituted, by $C_1$-$C_8$-alkyl, cyano, hydroxyl, amino, $C_1$-$C_6$-alkylamino, N,N-di-$C_1$-$C_6$-alkylamino, $C_2$-$C_6$-alkenyl, $C_2$-$C_6$-alkynyl, $C_0$-$C_6$-alkylcarbonylamino, $C_1$-$C_6$-alkoxycarbonyl-amino, halogen, trifluoromethyl, $C_1$-$C_8$-alkoxy, optionally N-mono- or N,N-di-$C_1$-$C_8$-alkylated carbamoyl, optionally esterified carboxyl, aryl or heterocyclyl, it being possible for the substituent to be in any position, for example in the o-, m- or p-position of the phenyl radical or in the 3- or 4-position of the 1- or 2-naphthyl radical and it also being possible for a plurality of identical or different substituents to be present. Preference is likewise given to aryl having 6-10 carbon atoms, in particular phenyl or 1- or 2-naphthyl with a $C_1$-$C_6$-alkylenedioxy radical.

Heterocyclyl contains generally 5 to 7 ring atoms in the heterocyclyl ring which preferably contains one ring nitrogen atom and one further ring heteroatom selected from oxygen, sulphur or nitrogen. Heterocyclyl is, for example, pyridinyl or imidazolyl. Heterocyclyl may be unsubstituted or mono- or polysubstituted, for example mono- or disubstituted, by $C_1$-$C_8$-alkyl, halogen, oxide, cyano, amino, $C_1$-$C_6$-alkylamino, di-$C_1$-$C_6$-alkylamino, oxo, trifluoromethyl, $C_1$-$C_8$-alkoxy, optionally N-mono- or N,N-di-$C_1$-$C_8$-alkylated carbamoyl, $C_1$-$C_8$-alkoxycarbonyl, aryl or heterocyclyl.

In the case of nitrogen heterocycles, the heterocyclyl radicals can be bonded either via the nitrogen or via a ring carbon.

Halogen is, for example, fluorine, chlorine, bromine or iodine, preferably fluorine and chlorine.

Polyhalo-$C_1$-$C_4$-alkyl is, for example, mono-, di-, tri- or tetrahalo-$C_1$-$C_4$-alkyl such as fluoromethyl or trifluoromethyl.

Polyhalo-$C_1$-$C_4$-alkoxy is, for example, mono-, di-, tri- or tetrahalo-$C_1$-$C_4$-alkoxy such as trifluoromethoxy.

3- to 8-membered cycloalkoxy is preferably 3-, 5- or 6-membered cycloalkoxy such as cyclopropyloxy, cyclopentyloxy and cyclohexyloxy.

3- to 8-membered cycloalkyl is preferably 3-, 5- or 6-membered cycloalkyl such as cyclopropyl, cyclopentyl and cyclohexyl.

$C_1$-$C_8$-Cycloalkyl-$C_1$-$C_6$-alkyl is, for example, cyclopropyl-$C_1$-$C_4$-alkyl, cyclobutyl-$C_1$-$C_4$-alkyl, cyclopentyl-$C_1$-$C_4$-alkyl or cyclohexyl-$C_1$-$C_4$-alkyl such as cyclopropylmethyl, cyclobutyl methyl, cyclopentyl methyl, cyclohexyl methyl, cyclopropylethyl, cyclobutylethyl, cyclopentylethyl and cyclohexylethyl Amino-$C_1$-$C_4$-alkoxy is, for example, 2-aminoethoxy, 3-aminopropyloxy or 4-aminobutyloxy.

Amino-$C_1$-$C_4$-alkyl is, for example, 2-aminoethyl, 3-aminopropyl or 4-aminobutyl.

Carbamoyl-$C_1$-$C_8$-alkyl is, for example, carbamoylmethyl, 2-carbamoylethyl, 3-carbamoyl-propyl, 2-(3-carbamoyl)propyl, 2-carbamoylpropyl, 3-(1-carbamoyl)propyl, 2-(2-carbamoyl)-propyl, 2-carbamoyl-2-methylpropyl, 4-carbamoylbutyl, 1-carbamoylbutyl, 1-(1-carbamoyl-2-methyl)butyl, 3-(4-carbamoyl-2-methyl)butyl.

Carboxy-$C_1$-$C_4$-alkoxy is, for example, carboxymethoxy, 2-carboxyethoxy, 2- or 3-carboxypropyloxy or 4-carboxybutyloxy, in particular carboxymethoxy.

Carboxy-$C_1$-$C_4$-alkyl is, for example, carboxymethyl, 2-carboxyethyl, 2- or 3-carboxypropyl, 2-carboxy-2-methylpropyl or 4-carboxybutyl, in particular carboxymethyl.

Cyano-$C_1$-$C_4$-alkoxy is, for example, cyanomethoxy, 2-cyanoethoxy, 2- or 3-cyanopropyloxy or 4-cyanobutyloxy, in particular cyanomethoxy.

Cyano-$C_1$-$C_4$-alkyl is, for example, cyanomethyl, 2-cyanoethyl, 2- or 3-cyanopropyl, 2-cyano-2-methylpropyl or 4-cyanobutyl, in particular cyanomethyl.

N,N-Di-$C_1$-$C_4$-alkylamino is, for example, dimethylamino, N-methyl-N-ethylamino, diethylamino, N-methyl-N-propylamino or N-butyl-N-methylamino.

N,N-Di-$C_1$-$C_4$-alkylamino-$C_1$-$C_4$-alkoxy is 2-dimethylaminoethoxy, 3-dimethylaminopropyloxy, 4-dimethylaminobutyloxy, 2-diethylaminoethoxy, 2-(N-methyl-N-ethylamino)ethoxy or 2-(N-butyl-N-methylamino)ethoxy.

N,N-Di-$C_1$-$C_4$-alkylamino-$C_1$-$C_4$-alkyl is, for example, 2-dimethylaminoethyl, 3-dimethyl-aminopropyl, 4-dimethylaminobutyl, 2-diethylaminoethyl, 2-(N-methyl-N-ethylamino)ethyl or 2-(N-butyl-N-methylamino)ethyl.

N,N-Di-$C_1$-$C_4$-alkylcarbamoyl-$C_1$-$C_4$-alkoxy is, for example, methyl- or dimethylcarbamoyl- $C_1$-$C_4$-alkoxy, such as N-methyl-, N-butyl- or N,N-dimethylcarbamoylmethoxy, 2-(N-methylcarbamoyl)ethoxy, 2-(N-butylcarbamoyl)ethoxy, 2-(N, N-dimethylcarbamoyl)ethoxy, 3-(N-methylcarbamoyl)propyloxy, 3-(N-butylcarbamoyl)propyloxy, 3-(N,N-dimethyl-carbamoyl)propyloxy or 4-(N-methylcarbamoyl)butyloxy, 4-(N-butylcarbamoyl)butyloxy or 4-(N,N-dimethylcarbamoyl)butyloxy, in particular N-methyl-, N-butyl- or N,N-dimethylcarbamoylmethoxy.

N,N-Di-$C_1$-$C_4$-alkylcarbamoyl-$C_1$-$C_4$-alkyl is, for example, 2-dimethylcarbamoylethyl, 3-dimethylcarbamoyl propyl, 2-dimethylcarbamoyl propyl, 2-(dimethylcarbamoyl)-2-methylpropyl or 2-(1-dimethylcarbamoyl)butyl.

Optionally partially hydrogenated pyridyl- or N-oxidopyridyl-$C_1$-$C_4$-alkoxy is, for example, pyridyl- or N-oxidopyridylmethoxy, 2-pyridylethoxy, 2- or 3-pyridylpropyloxy or 4-pyridylbutyloxy, in particular 3- or 4-pyridylmethoxy.

Optionally partially hydrogenated pyridyl- or N-oxidopyridyl-$C_1$-$C_4$-alkyl is, for example, pyridyl- or N-oxidopyridylmethyl, 2-pyridylethyl, 2- or 3-pyridylpropyl or 4-pyridylbutyl, in particular 3- or 4-pyridylmethyl.

Halo-$C_2$-$C_8$-(hydroxy)alkoxy is, for example, halo-$C_2$-$C_4$-(hydroxy)alkoxy such as 3-halo- or 3-chloro-2-hydroxypropyloxy.

Hydroxy-$C_2$-$C_8$-alkoxy is, for example, hydroxy-$C_2$-$C_4$-alkoxy such as 2-hydroxybutyloxy, 3-hydroxypropyloxy or 4-hydroxybutyloxy.

Hydroxy-$C_2$-$C_8$-alkyl is, for example, hydroxy-$C_2$-$C_4$-alkyl such as 2-hydroxyethyl, 3-hydroxy-propyl or 4-hydroxybutyl.

Morpholino-$C_1$-$C_4$-alkoxy may be N-oxidized and is, for example, 1-morpholinoethoxy, 3-morpholinopropyloxy or 1-(morpholino-2-methyl)propyloxy.

Morpholino-$C_1$-$C_4$-alkyl may be N-oxidized and is, for example, morpholinomethyl, 2-morpholinoethyl, 3-morpholinopropyl or 1- or 2-(4-morpholino)butyl.

$C_1$-$C_8$-Alkanoyl is in particular $C_2$-$C_6$-alkanoyl such as acetyl, propionyl, butyryl, isobutyryl or pivaloyl.

N-$C_1$-$C_4$-Alkanoylamino-$C_1$-$C_4$-alkyl is, for example, 2-acetaminoethyl.

$C_1$-$C_8$-Alkanoyl-$C_2$-$C_4$-alkoxy (oxo-$C_2$-$C_8$-alkoxy) bears the $C_1$-$C_8$-alkanoyl group in higher than the α-position and is, for example, 4-acetylbutoxy.

$C_1$-$C_8$-Alkanoyloxy-$C_1$-$C_4$-alkyl bears the $C_1$-$C_8$-alkanoyloxy group in higher than the α-position and is, for example, 4-acetoxybutyl.

$C_1$-$C_8$-Alkanesulphonyl-$C_1$-$C_4$-(hydroxy)alkoxy is, for example, 3-methanesulphonyl-2-hydroxypropyloxy.

$C_1$-$C_8$-Alkanesulphonyl-$C_1$-$C_4$-alkoxy is, for example, methanesulphonylmethoxy or 3-methanesulphonyl-2-hydroxypropyloxy.

$C_1$-$C_8$-Alkanesulphonylamino-$C_1$-$C_4$-alkoxy is, for example, ethanesulphonylaminomethoxy, 2-ethanesulphonylaminoethoxy, 3-ethanesulphonylaminopropyloxy or 3-(1,1-dimethylethane-sulphonylamino)propyloxy.

$C_1$-$C_4$-Alkanesulphonylamino-$C_1$-$C_4$-alkyl is, for example, ethanesulphonylaminomethyl, 2-ethanesulphonylaminoethyl, 3-ethanesulphonylaminopropyl or 3-(1,1-dimethylethane-sulphonylamino)propyl.

$C_1$-$C_8$-Alkanesulphonyl-$C_1$-$C_4$-alkyl is, for example, ethanesulphonylmethyl, 2-ethane-sulphonylethyl, 3-ethanesulphonylpropyl or 3-(1,1-dimethylethanesulphonyl)propyl.

$C_2$-$C_8$-Alkenyloxy is, for example, allyloxy.

$C_2$-$C_8$-Alkenyloxy-$C_1$-$C_4$-alkoxy is, for example, allyloxymethoxy.

$C_2$-$C_8$-Alkenyloxy-$C_1$-$C_4$-alkyl is, for example, allyloxymethyl.

$C_1$-$C_8$-Alkoxy is, for example, Cl-$C_5$-alkoxy such as methoxy, ethoxy, propyloxy, isopropyloxy, butyloxy, isobutyloxy, sec-butyloxy, tert-butyloxy or pentyloxy, but may also be a hexyloxy or heptyloxy group.

$C_1$-$C_8$-Alkoxycarbonyl is preferably $C_2$-$C_5$-alkoxycarbonyl such as methoxycarbonyl, ethoxycarbonyl, propyloxycarbonyl, isopropyloxycarbonyl, butyloxycarbonyl, isobutyloxycarbonyl, sec-butyloxycarbonyl or tert-butyloxycarbonyl.

$C_1$-$C_8$-Alkoxycarbonylamino-$C_2$-$C_8$-alkoxy is preferably $C_2$-$C_5$-alkoxycarbonylamino-$C_2$-$C_8$-alkoxy such as methoxycarbonylamino-$C_2$-$C_8$-alkoxy, ethoxycarbonylamino-$C_2$-$C_8$-alkoxy, propyloxycarbonylamino-$C_2$-$C_8$-alkoxy, isopropyloxycarbonylamino-$C_2$-$C_8$-alkoxy, butyloxycarbonylamino-$C_2$-$C_8$-alkoxy, isobutyloxycarbonylamino-$C_2$-$C_8$-alkoxy, sec-butyloxycarbonylamino-$C_2$-$C_8$-alkoxy or tert-butyloxycarbonylamino-$C_2$-$C_8$-alkoxy, in which $C_2$-$C_8$-alkoxy is, for example, ethoxy, propyloxy, butyloxy, pentyloxy or hexyloxy.

$C_1$-$C_8$-Alkoxycarbonylamino-$C_2$-$C_8$-alkyl is preferably $C_2$-$C_5$-alkoxycarbonylamino-$C_2$-$C_8$-alkyl such as methoxycarbonylamino-$C_2$-$C_8$-alkyl, ethoxycarbonylamino-$C_2$-$C_8$-alkyl, propyloxycarbonylamino-$C_2$-$C_8$-alkyl, isopropyloxycarbonylamino-$C_2$-$C_8$-alkyl, butyloxycarbonylamino-$C_2$-$C_8$-alkyl, isobutyloxycarbonylamino-$C_2$-$C_8$-alkyl, sec-butyloxycarbonylamino-$C_2$-$C_8$-alkyl or tert-butyloxycarbonylamino-$C_2$-$C_8$-alkyl, in which $C_2$-$C_8$-alkyl is, for example, ethyl, propyl, butyl, pentyl or hexyl.

$C_1$-$C_4$-Alkoxycarbonyl-$C_1$-$C_4$-alkoxy is, for example, methoxycarbonyl- or ethoxycarbonylmethoxy, 2-methoxycarbonyl- or 2-ethoxycarbonylethoxy, 2- or 3-methoxycarbonyl- or 2- or 3-ethoxycarbonylpropyloxy or 4-methoxycarbonyl- or 4-ethoxycarbonylbutyloxy, in particular methoxycarbonyl- or ethoxycarbonylmethoxy or 3-methoxycarbonyl- or 3-ethoxycarbonylpropyloxy.

$C_1$-$C_4$-Alkoxycarbonyl-$C_1$-$C_4$-alkyl is, for example, methoxycarbonyl- or ethoxycarbonylmethyl, 2-methoxycarbonyl- or 2-ethoxycarbonylethyl, 3-methoxycarbonyl- or 3-ethoxycarbonylpropyl or 4-ethoxycarbonyl butyl.

$C_1$-$C_4$-Alkoxy-$C_2$-$C_4$-alkenyl is, for example 4-methoxybut-2-enyl.

$C_1$-$C_8$-Alkoxy-$C_1$-$C_8$-alkoxy is, for example, 2-methoxy-, 2-ethoxy- or 2-propyloxyethoxy, 3-methoxy- or 3-ethoxypropyloxy or 4-methoxybutyloxy, in particular 3-methoxypropyloxy or 4-methoxybutyloxy.

$C_1$-$C_4$-Alkoxy-$C_1$-$C_4$-alkoxy-$C_1$-$C_4$-alkyl is, for example, 2-methoxy-, 2-ethoxy- or 2-propyloxyethoxymethyl, 2-(2-methoxy-, 2-ethoxy- or 2-propyloxyethoxy)ethyl, 3-(3-methoxy- or 3-ethoxypropyloxy)propyl or 4-(2-methoxybutyloxy)butyl, in particular 2-(3-methoxypropyloxy)ethyl or 2-(4-methoxybutyloxy)ethyl.

$C_1$-$C_4$-Alkoxy-$C_1$-$C_4$-alkyl is, for example, ethoxymethyl, propyloxymethyl, butyloxymethyl, 2-methoxy-, 2-ethoxy- or 2-propyloxyethyl, 3-methoxy- or 3-ethoxypropyl or 4-methoxybutyl, in particular 3-methoxypropyl or 4-methoxybutyl.

$C_1$-$C_8$-Alkyl may be straight-chain or branched and/or bridged and is, for example, methyl, ethyl, propyl, isopropyl, butyl, isobutyl, sec-butyl, tert-butyl, or a pentyl, hexyl or heptyl group.

$C_2$-$C_8$-Alkenyl may be straight-chain or branched and is, for example, vinyl, allyl, propenyl, isopropenyl, butenyl, isobutenyl or a pentenyl, hexenyl or heptenyl group.

$C_2$-$C_6$-Alkynyl may be straight-chain or branched and is, for example, ethynyl, 1-propnyl, 3-propnyl, 1-butnyl, 3-butnyl, 4-butnyl or a pentnyl or hexnyl group.

$C_1$-$C_4$-Alkylamino is, for example, methylamino, ethylamino, propylamino or butylamino.

$C_1$-$C_4$-Alkylamino-$C_1$-$C_4$-alkoxy is, for example, propylaminomethoxy, 2-methylamino-, 2-ethylamino-, 2-propylamino- or 2-butylaminoethoxy, 3-ethylamino- or 3-propylaminopropyloxy or 4-methylaminobutoxy.

$C_1$-$C_4$-Alkylamino-$C_1$-$C_4$-alkyl is, for example, propylaminomethyl, 2-methylamino-, 2-ethylamino-, 2-propylamino- or 2-butylaminoethyl, 3-ethylamino- or 3-propylaminopropyl or 4-methylaminobutyl.

N-$C_1$-$C_8$-Alkylcarbamoyl-$C_1$-$C_4$-alkoxy is, for example, methyl- or dimethylcarbamoyl-$C_1$-$C_4$-alkoxy, e.g. methylcarbamoylmethoxy, 2-methylcarbamoylethoxy or 3-methylcarbamoyl-propyloxy.

$C_0$-$C_6$-Alkylcarbonylamino is, for example, carbonylamino, methylcarbonylamino, ethylcarbonylamino or propylcarbonylamino.

$C_1$-$C_6$-Alkylenedioxy is, for example, methylenedioxy or ethylenedioxy, but may also be 1,3- or 1,2-propylenedioxy.

$C_1$-$C_4$-Alkylthio-$C_1$-$C_4$-(hydroxy)alkoxy is, for example, 2-hydroxy-3-methylthiopropyloxy.

$C_1$-$C_4$-Alkylthio-$C_1$-$C_4$-alkoxy is, for example, methylthio-$C_1$-$C_4$-alkoxy, e.g. methylthio-methoxy, 2-methylthioethoxy or 3-methylthiopropyloxy.

$C_1$-$C_4$-Alkylthio-$C_1$-$C_4$-alkyl is, for example, methylthio-$C_1$-$C_4$-alkyl, e.g. methylthiomethyl, 2-methylthioethyl or 3-methylthiopropyl.

N'—$C_2$-$C_8$-Alkanoylpiperazino-$C_1$-$C_4$-alkyl is, for example, 4-acetylpiperazinomethyl.

N'—$C_1$-$C_4$-Alkylpiperazino-$C_1$-$C_4$-alkyl is 4-methylpiperazinomethyl.

Piperazino-$C_1$-$C_4$-alkyl is, for example, piperazinomethyl, 2-piperazinoethyl or 3-piperazinopropyl.

Piperidino-$C_1$-$C_4$-alkoxy is, for example, piperidinomethoxy, 2-piperidinoethoxy or 3-piperidinopropyloxy.

Piperidino-$C_1$-$C_4$-alkyl is, for example, piperidinomethyl, 2-piperidinoethyl or 3-piperidinopropyl.

Pyrrolidino-$C_2$-$C_4$-alkoxy is, for example, 2-pyrrolidinoethoxy or 3-pyrrolidinopropyloxy.

Pyrrolidino-$C_1$-$C_4$-alkyl is, for example, pyrrolidino-$C_1$-$C_4$-alkyl such as pyrrolidinomethyl, 2-pyrrolidinoethyl or 3-pyrrolidinopropyl.

S,S-Dioxothiomorpholino-$C_1$-$C_4$-alkyl is, for example, S,S-dioxothiomorpholinomethyl or 2-(S,S-dioxo)thiomorpholinoethyl.

S-Oxothiomorpholino-$C_1$-$C_4$-alkyl is, for example, S-oxothiomorpholinomethyl or 2-(S-oxo)thiomorpholinoethyl.

Thiazolyl-$C_1$-$C_4$-alkoxy is, for example, thiazolylmethoxy, 2-thiazolylethoxy or 3-thiazolyl propyloxy.

Thiomorpholino-$C_1$-$C_4$-alkyl or S,S-dioxothiomorpholino-$C_1$-$C_4$-alkyl is, for example, thiomorpholino-$C_1$-$C_4$-alkyl such as -methyl or -ethyl, or S,S-dioxothiomorpholino-$C_1$-$C_4$-alkyl such as -methyl or -ethyl.

Optionally N-mono- or N,N-di-$C_1$-$C_8$-alkylated carbamoyl is, for example, carbamoyl, methylcarbamoyl, ethylcarbamoyl, N,N-dimethylcarbamoyl, N,N-diethylcarbamoyl or propylcarbamoyl.

Optionally esterified carboxyl is, for example, carboxyl esterified with $C_0$-$C_6$-alkyl, such as carboxyl or $C_1$-$C_6$-alkoxycarbonyl.

Depending on the presence of asymmetric carbon atoms, the inventive compounds may be present in the form of isomer mixtures, especially as racemates, or in the form of pure isomers, especially of optical antipodes. The invention encompasses all of these forms. Diastereomer mixtures, diastereomeric racemates or mixtures of diastereomeric racemates may be separated by customary methods, for example by column chromatography, thin-layer chromatography, HPLC and the like.

Salts of compounds having salt-forming groups are in particular acid addition salts, salts with bases or, in the presence of a plurality of salt-forming groups, in some cases also mixed salts or internal salts.

Salts are primarily the pharmaceutically usable or nontoxic salts of compounds of the formula (I). Such salts are formed, for example, from compounds of the formula (I) with an acidic group, for example a carboxyl or sulpho group, and are, for example, the salts thereof with suitable bases, such as nontoxic metal salts derived from metals of group Ia, Ib, IIa and IIb of the Periodic Table of the Elements, for example alkali metal, in particular lithium, sodium or potassium salts, alkaline earth metal salts, for example magnesium or calcium salts, and also zinc salts or ammonium salts, including those salts which are formed with organic amines, such as optionally hydroxy-substituted mono-, di- or trialkylamines, in particular mono-, di- or tri(lower alkyl)amines, or with quaternary ammonium bases, for example methyl-, ethyl-, diethyl- or triethylamine, mono-, bis- or tris(2-hydroxy(lower alkyl)) amines, such as ethanol-, diethanol- or triethanolamine, tris (hydroxymethyl)methylamine or 2hydroxy-tert-butylamine, N,N-di(lower alkyl)-N-(hydroxy(lower alkyl))amine, such as N,N-dimethyl-N-(2-hydroxyethyl)amine, or N-methyl-D-glucamine, or quaternary ammonium hydroxides, such as tetrabutylammonium hydroxide. The compounds of the formula I having a basic group, for example an amino group, may form acid addition salts, for example with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic, sulpho or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the α-amino acids mentioned above, and also methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose-6-phosphate, N-cyclohexylsulphamic acid (with formation of cyclamates) or with other acidic organic compounds such as ascorbic acid. Compounds of the formula (I) with acidic and basic groups may also form internal salts.

For the isolation and purification, pharmaceutically unsuitable salts may also find use.

The compounds of the formula (I) also include those compounds in which one or more atoms are replaced by their stable, non-radioactive isotopes; for example, a hydrogen atom by deuterium.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically usable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)alkyl esters or such as lower α-(alkanoyloxy, alkoxycarbonyl or dialkylaminocarbonyl)alkyl esters; as such, pivaloyloxymethyl esters and similar esters are utilized in a conventional manner.

Owing to the close relationship between a free compound, a prodrug derivative and a salt compound, a certain compound in this invention also encompasses its prodrug derivative and salt form, where this is possible and appropriate.

The compound groups mentioned below are not to be regarded as closed, but rather parts of these compound groups may be exchanged with one another or with the definitions given above or omitted in a sensible manner, for example to replace general by more specific definitions.

The invention preferably relates to compounds of the formula (I), in which $R_1$ is aryl which is optionally mono- or polysubstituted by $C_1$-$C_8$-alkyl, cyano, hydroxyl, amino, $C_1$-$C_6$-alkylamino, N,N-di-$C_1$-$C_6$-alkylamino, $C_2$-$C_6$-alkenyl, $C_2$-$C_6$-alkynyl, $C_0$-$C_6$-alkylcarbonyl-amino, $C_1$-$C_6$-alkoxycarbonylamino, halogen, trifluoromethyl, $C_1$-$C_8$-alkoxy, optionally N-mono- or N,N-di-$C_1$-$C_8$-alkylated carbamoyl, optionally esterified carboxyl, aryl or heterocyclyl;

$R_2$ is $C_1$-$C_8$-alkyl; $R_3$ is hydrogen;
$R_4$ is hydrogen;
$R_5$ are each independently hydrogen or $C_1$-$C_8$-alkyl;
$R_6$ is hydrogen;
R are each independently 1-4 radicals selected from:
hydrogen, halogen, $C_1$-$C_4$-alkyl, $C_1$-$C_4$-alkoxy-$C_1$-$C_4$-alkyl, Cl-$C_4$-alkoxy-$C_1$-$C_4$-alkoxy-$C_1$-$C_4$-alkyl, $C_1$-$C_8$-alkoxy and $C_1$-$C_4$-alkoxy-$C_1$-$C_4$-alkoxy;
and their pharmaceutically usable salts.

Preference is likewise given to compounds of the formula (I) in which
$R_1$ is aryl substituted by $C_1$-$C_6$-alkylenedioxy;
$R_2$ is $C_1$-$C_8$-alkyl;
$R_3$ is hydrogen;
$R_4$ is hydrogen;
$R_5$ are each independently hydrogen or $C_1$-$C_8$-alkyl;
$R_6$ is hydrogen;
R are each independently 1-4 radicals selected from:
hydrogen, halogen, $C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$- alkyl, $C_1$-$C_8$-alkoxy and $C_1$-$C_4$-alkoxy-$C_1$-$C_4$-alkoxy;
and their pharmaceutically usable salts.

Preference is likewise given to compounds of the formula (I) in which
$R_2$ is $C_1$-$C_8$-alkyl;
$R_3$ is hydrogen;
$R_4$ is hydrogen;
$R_5$ are each independently hydrogen or $C_1$-$C_8$-alkyl;
$R_6$ is hydrogen; and
R are each independently 1-4 radicals selected from:
hydrogen, halogen, $C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy and $C_1$-$C_4$-alkoxy-$C_1$-$C_4$-alkoxy.

Preference is likewise given to compounds of the formula (I) in which $R_2$ is $C_1$-$C_8$-alkyl.

Preference is likewise given to compounds of the formula (I) in which $R_3$ is hydrogen.

Preference is likewise given to compounds of the formula (I) in which $R_4$ is hydrogen.

Preference is likewise given to compounds of the formula (I) in which $R_5$ are each independently hydrogen or $C_1$-$C_8$-alkyl, particular preference being given to one $R_5$ radical being hydrogen and one $R_5$ radical being $C_1$-$C_8$-alkyl.

Preference is likewise given to compounds of the formula (I) in which $R_6$ is hydrogen.

Preference is likewise given to compounds of the formula (I) in which R are each independently 1-4 radicals selected from:

hydrogen, halogen, $C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy and $C_1$-$C_4$-alkoxy-$C_1$-$C_4$-alkoxy.

The invention further preferably relates to compounds of the formula

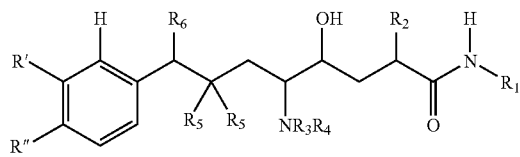

(I')

in which $R_1$, $R_2$, $R_3$, $R_4$, $R_5$ and $R_6$ are each as defined for the compounds of the formula (I) and stereochemistry shown in formula (IA) (each "S"), the substituents each being as defined above, and their pharmaceutically usable salts.

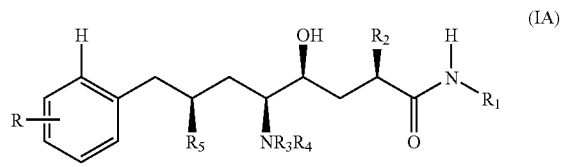

(IA)

The compounds of the formula (I) or formula (IA) may be prepared analogously to the literature preparation processes (see WO 2002/008172 and WO 2002/002508 or literature cited there) (scheme).

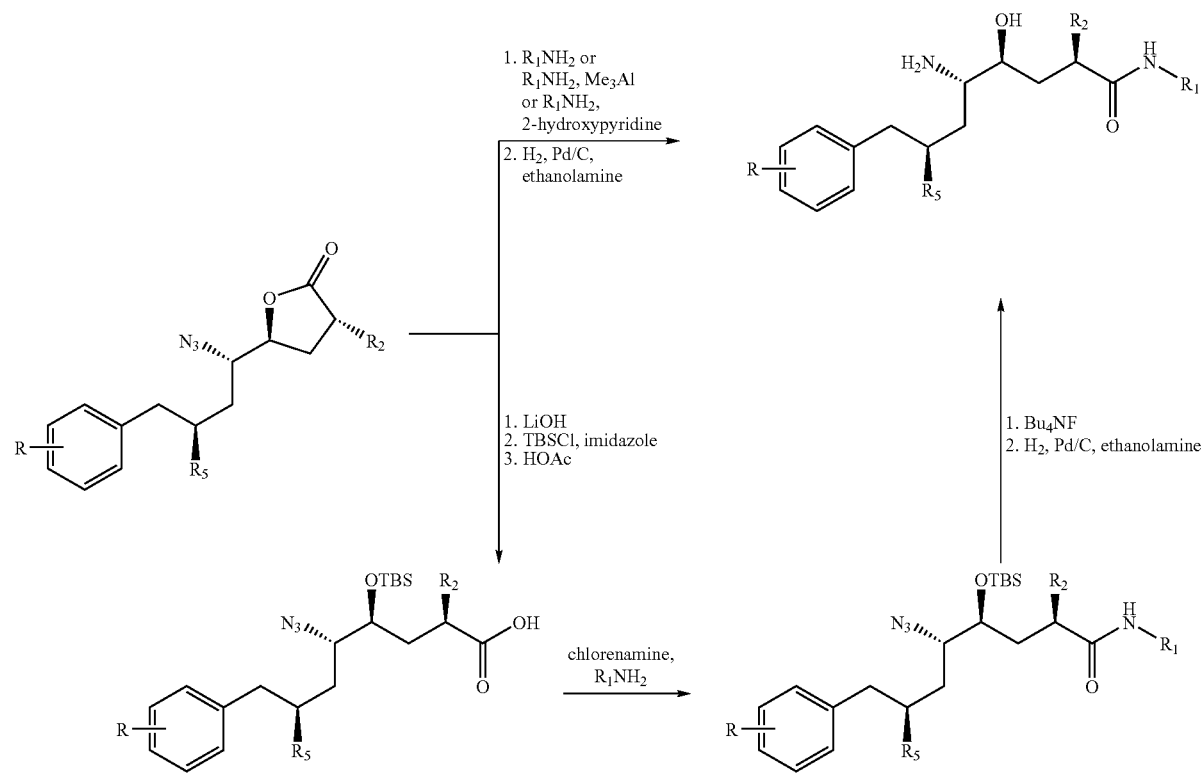

Details of the specific preparation variants can be taken from the examples.

R' and R" are each independently as defined for R for the compounds of the formula (I) and are preferably hydrogen, halogen, $C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy or $C_1$-$C_4$-alkoxy-$C_1$-$C_4$-alkoxy.

Particular preference is given in each case to those compounds of the formula (I) in which at least one asymmetric carbon atom, for example one, two, three or preferably all four asymmetric carbon atoms, of the main chain have the The compounds of the formula (I) may also be prepared in optically pure form. The separation into antipodes may be effected by methods known per se, either preferably at a synthetically early stage by salt formation with an optically active acid, for example (+)- or (−)-mandelic acid and separation of the diastereomeric salts by fractional crystallization, or preferably at a rather later stage by derivatization with a chiral auxiliary building block, for example (+)- or (−)-camphanoyl chloride, and separation of the diastereomeric products by chromatography and/or crystallization and subsequent cleavage of the bond to the chiral auxiliary. To determine the absolute configuration of the compound present, the pure diastereomeric salts and derivatives may be analysed with common spectroscopic methods, of which X-ray spectroscopy on single crystals constitutes a particularly suitable method.

The compounds of the formula (I) or of the formula (IA), and the pharmaceutically usable salts thereof, have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the release of the hormone aldosterone which inhibits the release of the sodium ions from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

One experimental method of detecting the action of renin inhibitors is by means of in vitro tests, in which the reduction of the formation of angiotensin I in different systems (human plasma, purified human renin together with synthetic or natural renin substrate) is measured. One in vitro test which is used is the one according to Nussberger et al. (1987) J. Cardiovascular Pharmacol., Vol. 9, p. 39-44 which follows. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-6}$ to about $10^{-10}$ mol/l.

In salt-depleted animals, renin inhibitors bring about a blood pressure decrease. Human renin differs from renin of other species. To test inhibitors of human renin, primates (marmosets, Callithrixjacchus) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[(2-furanyl methyl)amino]benzoic acid) (5 mg/kg). 16 hours after the injection of furosemide, the test substances are administered either directly into the femoral artery by means of an injection cannula or into the stomach by gavage as a suspension or solution, and their effect on blood pressure and heart rate is evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the formula (I), or preferably of the formula (IA), and the pharmaceutically usable salts thereof, may find use as medicaments, for example in the form of pharmaceutical preparations. The pharmaceutical preparations may be administered enterally, such as orally, for example in the form of tablets, coated tablets, sugar-coated tablets, hard and soft gelatin capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatin capsules, the compounds of the formula (I), or preferably of the formula (IA), and pharmaceutically usable salts thereof may be processed with pharmaceutically inert, inorganic or organic excipients. Such excipients used, for example for tablets, coated tablets and hard gelatin capsules, may be lactose, corn starch, or derivatives thereof, talc, stearic acid or salts thereof etc.

Suitable excipients for soft gelatin capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formula (I), or preferably of the formula (IA), and the pharmaceutically usable salts thereof, in the treatment or prevention of hypertension, heart failure, glaucoma, myocardial infarction, kidney failure, restenoses or stroke.

The compounds of the formula (I), or preferably of the formula (IA), and the pharmaceutically usable salts thereof may also be administered in combination with one or more agents having cardiovascular action, for example α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyidopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formula (I) or (IA) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The examples which follow illustrate the present invention. All temperatures are reported in degrees Celsius, pressures in mbar. Unless stated otherwise, the reactions take place at room temperature. The abbreviation "Rf=xx(A)" means, for example, that the Rf value xx is determined in the solvent system A. The ratio of solvents relative to one another is always reported in parts by volume. Chemical names for end products and intermediates were generated on the basis of the structural formulae with the aid of the program AutoNom 2000 (automatic nomenclature).

HPLC gradients on Hypersil BDS C-18 (5 um); column: 4×125 mm

I 90% water*/10% acetonitrile* to 0% water*/100% acetonitrile* in 5 minutes +2.5 minutes (1.5 ml/min)

II 95% water*/5% acetonitrile* to 0% water*/100% acetonitrile* in 40 minutes (0.8 ml/min)

* contains 0.1% trifluoroacetic acid

The following abbreviations are used:

Rf ratio of distance travelled by a substance to separation of the eluent front from the start point in thin-layer chromatography Rt retention time of a substance in HPLC (in minutes)

m.p. melting point (temperature)

General Method A: (Azide Reduction)

A solution of 1 mmol of "azide derivative" in 10-20 ml of ethanol and ethanolamine (1 equiv.) is hydrogenated in the presence of 200-400 mg of 10% Pd/C (moist) at 0° C. over 1-3 hours. The reaction mixture is clarified by filtration and the catalyst is washed with ethanol. The filtrate is concentrated by evaporation. The title compound is obtained from the residue by means of flash chromatography ($SiO_2$ 60 F).

General Method B: (Lactone Amidation I)

A mixture of 1 mmol of "lactone", "amine" (10-30 equiv.) and 2-hydroxypyridine (1 equiv.) is stirred at 65° C. over 2-24 hours. The reaction mixture is cooled to room temperature, concentrated by evaporation, admixed ith 1 M aqueous sodium hydrogencarbonate solution and extracted with tert-butyl methyl ether (2×). The combined organic phases are washed with water and brine, dried over sodium sulphate and concentrated. The title compound is obtained from the residue by means of flash chromatography ($SiO_2$ 60 F).

General Method C: (Lactone Amidation II)

A solution of 1.1 mmol of trimethylaluminium solution (2 M in heptane) at −78° C. is admixed with a solution of 1.2 mmol of "amine" in 1-2 ml of toluene. The reaction mixture is warmed to room temperature, stirred for a further 30-60 minutes and subsequently concentrated by evaporation. The residue is admixed with a solution of 1 mmol of "lactone" in 2 ml of toluene and stirred at 80° C. for 2-4 hours. The reaction mixture is cooled to room temperature, admixed with 10 ml of 1 N HCl and then stirred for a further 30 minutes. The reaction mixture is diluted with brine and extracted with toluene (2×)—the combined organic phases are dried over sodium sulphate and concentrated by evaporation. The title compound is obtained from the residue by means of flash chromatography ($SiO_2$ 60 F).

EXAMPLE 1

N-Phenyl-5(S)-amino-4(S)-hydroxy-2(S)-isopropyl-7(S)-[4-methoxy-3-(3-methoxypropoxy)benzyl]-8-methylnonanamide Analogously to Method A, 0.132 g of N-phenyl-5(S)-azido-4(S)-hydroxy-2(S)-isopropyl-7(S)-[4-methoxy-3-(3-methoxypropoxy)benzyl]-8-methylnonanamide is used to prepare the title compound as a colourless foam. Rf=0.45 (200:20:1 dichloromethane-methanol-25% conc. ammonia); Rt=4.36 minutes (gradient I).

The starting material is prepared as follows:

a) N-Phenyl-5(S)-azido-4(S)-hydroxy-2(S)-isopropyl-7(S)-[4-methoxy-3-(3-methoxypropoxy)benzyl]-8-methylnonanamide Analogously to Method C, 0.466 g of 5(S)-{1(S)-azido-3(S)-[4-methoxy-3-(3-methoxypropoxy)benzyl]-4-methylpentyl}-3(S)-isopropyidihydrofuran-2-one [324763-46-4] and 0.11 ml of aniline are reacted. The title compound is obtained as a colourless oil. Rf=0.53 (2:1 EtOAc-heptane); Rt=5.41 minutes (gradient I).

The process described in Example 1 is used analogously to prepare the following compounds:

EXAMPLES

2

N-(2-Fluorophenyl)-5(S)-amino-4(S)-hydroxy-2(S)-isopropyl-7(S)-[4-methoxy-3-(3-methoxypropoxy)benzyl]-8-methylnonanamide

3

N-(3-Fluorophenyl)-5(S)-amino-4(S)-hydroxy-2(S)-isopropyl-7(S)-[4-methoxy-3-(3-methoxypropoxy)benzyl]-8-methylnonanamide

4

N-(4-Fluorophenyl)-5(S)-amino-4(S)-hydroxy-2(S)-isopropyl-7(S)-[4-methoxy-3-(3-methoxypropoxy)benzyl]-8-methylnonanamide

5

N-(4-methoxyphenyl)-5(S)-amino-4(S)-hydroxy-2(S)-isopropyl-7(S)-[4-methoxy-3-(3-methoxypropoxy)benzyl]-8-methylnonanamide

6

N-(2-methoxyphenyl)-5(S)-amino-4(S)-hydroxy-2(S)-isopropyl-7(S)-[4-methoxy-3-(3-methoxypropoxy)benzyl]-8-methylnonanamide

7

N-(3-methoxyphenyl)-5(S)-amino-4(S)-hydroxy-2(S)-isopropyl-7(S)-[4-methoxy-3-(3-methoxypropoxy)benzyl]-8-methylnonanamide

8

N-(2-Cyanophenyl)-5(S)-amino-4(S)-hydroxy-2(S)-isopropyl-7(S)-[4-methoxy-3-(3-methoxypropoxy)benzyl]-8-methylnonanamide

9

N-(3-Cyanophenyl)-5(S)-amino-4(S)-hydroxy-2(S)-isopropyl-7(S)-[4-methoxy-3-(3-methoxypropoxy)benzyl]-8-methylnonanamide

10

N-(4-Cyanophenyl)-5(S)-amino-4(S)-hydroxy-2(S)-isopropyl-7(S)-[4-methoxy-3-(3-methoxypropoxy)benzyl]-8-methylnonanamide

11

N-(Benzo[1,3]dioxol-5-yl)-5(S)-amino-4(S)-hydroxy-2(S)-isopropyl-7(S)-[4-methoxy-3-(3-methoxypropoxy)benzyl]-8-methylnonanamide

12

N-(Benzo[1,3]dioxol-4-yl)-5(S)-amino-4(S)-hydroxy-2(S)-isopropyl-7(S)-[4-methoxy-3-(3-methoxypropoxy)benzyl]-8-methylnonanamide

13

N-(2,3-Dihydrobenzo[1,4]dioxin-6-yl)-5(S)-amino-4(S)-hydroxy-2(S)-isopropyl—7(S)-[4-methoxy-3-(3-methoxypropoxy)benzyl]-8-methylnonanamide

14

N-(2,3-Dihydrobenzo[1,4]dioxin-5-yl)-5(S)-amino-4(S)-hydroxy-2(S)-isopropyl-7(S)-[4-methoxy-3-(3-methoxypropoxy)benzyl]-8-methylnonanamide

The invention claimed is:
1. Compound of the formula

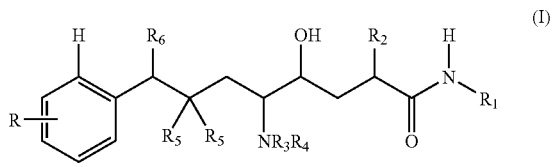

(I)

in which
R$_1$ is optionally substituted aryl;
R$_2$ is C$_1$-C$_8$-alkyl, C$_2$-C$_8$-alkenyl or C$_3$-C$_8$-cycloalkyl or is phenyl- or naphthyl-C$_1$-C$_4$-alkyl, each of which is unsubstituted or mono-, di- or trisubstituted by C$_1$-C$_4$-alkyl, C$_1$-C$_4$-alkoxy, hydroxyl, C$_1$-C$_4$-alkylamino, N,N-di-C$_1$-C$_4$-alkylamino, halogen and/or trifluoromethyl;
R$_3$ is hydrogen, C$_1$-C$_4$-alkyl or C$_1$-C$_8$-alkanoyl;
R$_4$ is hydrogen, C$_1$-C$_4$-alkyl or C$_1$-C$_8$-alkanoyl;
R$_5$ are each independently hydrogen, C$_1$-C$_8$-alkyl or, together with the carbon atom to which they are bonded, a C$_3$-C$_8$-cycloalkylidene radical;
R$_6$ is hydrogen or hydroxyl;
R are each independently 1-4 radicals selected from;
hydrogen, halogen, C$_1$-C$_8$-alkyl, 3- to 8-membered cycloalkyl, polyhalo-C$_1$-C$_4$-alkyl, polyhalo-C$_1$-C$_4$-alkoxy, C$_1$-C$_4$-alkoxy-C$_1$-C$_4$-alkyl, C$_1$-C$_4$-alkoxy-C$_1$-C$_4$-alkoxy-C$_1$-C$_4$-alkyl, 3- to 8-membered cycloalkoxy-C$_1$-C$_4$-alkyl, hydroxyl, C$_1$-C$_8$-alkanoyloxy-C$_1$-C$_4$-alkyl, hydroxy-C$_2$-C$_8$-alkyl, C$_1$-C$_4$-alkylthio-C$_1$-C$_4$-alkyl, C$_1$-C$_8$-alkanesulphonyl-C$_1$-C$_4$-alkyl, thiazolylthio-C$_1$-C$_4$-alkyl, thiazolinylthio-C$_1$-C$_4$-alkyl, imidazolylthio-C$_1$-C$_4$-alkyl, optionally N-oxidized pyridylthio-C$_1$-C$_4$-alkyl, pyrimidinylthio-C$_1$-C$_4$-alkyl, optionally partially hydrogenated pyridyl- or N-oxidopyridyl-C$_1$-C$_4$-alkyl, C$_1$-C$_4$-alkanesulphonylamino-C$_1$-C$_4$-alkyl, trifluoro-C$_1$-C$_8$-alkanesulphonylamino-C$_1$-C$_4$-alkyl, pyrrolidino-C$_1$-C$_4$-alkyl, piperidino-C$_1$-C$_4$-alkyl, piperazino-C$_1$-C$_4$-alkyl, N'-C$_1$-C$_4$-alkylpiperazino-C$_1$-C$_4$-alkyl, N'-C$_2$-C$_8$-alkanoylpiperazino-C$_1$-C$_4$-alkyl, morpholino-C$_1$-C$_4$-alkyl, thiomorpholino-C$_1$-C$_4$-alkyl, S-oxothiomorpholino-C$_1$-C$_4$-alkyl, S,S-dioxothiomorpholino-C$_1$-C$_4$-alkyl, cyano-C$_1$-C$_4$-alkyl, carboxy-C$_1$-C$_4$-alkyl, C$_1$-C$_4$-alkoxycarbonyl-C$_1$-C$_4$-alkyl, carbamoyl-C$_1$-C$_8$-alkyl, N-mono- or N,N-di-C$_1$-C$_4$-alkylcarbamoyl-C$_1$-C$_4$-alkyl, optionally by C$_1$-C$_4$-alkyl, C$_1$-C$_4$-alkoxy, hydroxyl, C$_1$-C$_4$-alkylamino, di-C$_1$-C$_4$-alkylamino, halogen and/or trifluoromethyl mono-, di- or trisubstituted phenyl, optionally by C$_1$-C$_4$-alkyl, C$_1$-C$_4$-alkoxy, hydroxyl, C$_1$-C$_4$-alkylamino, di-C$_1$-C$_4$-alkylamino, halogen and/or trifluoromethyl mono-, di- or trisubstituted naphthyl, hydroxy-C$_2$-C$_8$-alkoxy, halo-C$_2$-C$_8$-(hydroxy)alkoxy, C$_1$-C$_8$-alkanesulphonyl-C$_1$-C$_4$-(hydroxy)alkoxy, amino-C$_1$-C$_4$-alkyl, C$_1$-C$_4$-alkylamino-C$_1$-C$_4$-alkyl, N,N-di-C$_1$-C$_4$-alkylamino-C$_1$-C$_4$-alkyl, N—C$_1$-C$_4$-alkanoylamino-C$_1$-C$_4$-alkyl, C$_1$-C$_8$-alkoxycarbonylamino-C$_2$-C$_8$-alkyl, amino-C$_1$-C$_4$-alkoxy, C$_1$-C$_4$-alkylamino-C$_1$-C$_4$-alkoxy, N,N-di-C$_1$-C$_4$-alkylamino-C$_1$-C$_4$-alkoxy, C$_1$-C$_8$-alkanoylamino-C$_1$-C$_4$-alkoxy, C$_1$-C$_8$-alkoxycarbonylamino-C$_2$-C$_8$-alkoxy, C$_1$-C$_8$-alkanoyl-C$_2$-C$_4$-alkoxy which bears the alkanoyl group in higher than the α-position, C$_1$-C$_8$-alkoxy, 3- to 8-membered cycloalkoxy, C$_2$-C$_8$-alkenyloxy, 3- to 8-membered cycloalkoxy-C$_1$-C$_4$-alkoxy, C$_1$-C$_4$-alkoxy-C$_1$-C$_4$-alkoxy, C$_1$-C$_4$-alkoxy-C$_2$-C$_4$-alkenyl, C$_2$-C$_8$-alkenyloxy-C$_1$-C$_4$-alkoxy, C$_1$-C$_4$-alkoxy-C$_2$-C$_4$-alkenyloxy, C$_2$-C$_8$-alkenyloxy-C$_1$-C$_4$-alkyl, C$_1$-C$_4$-alkylthio-C$_1$-C$_4$-alkoxy, C$_1$-C$_8$-alkanesulphonyl-C$_1$-C$_4$-alkoxy, C$_1$-C$_4$-alkylthio-C$_1$-C$_4$-(hydroxy)alkoxy, optionally by C$_1$-C$_4$-alkyl, C$_1$-C$_4$-alkoxy, hydroxyl, C$_1$-C$_4$-alkylamino, di-C$_1$-C$_4$-alkylamino, halogen and/or trifluoromethyl mono-, di- or trisubstituted phenyl-C$_1$-C$_4$-alkoxy, optionally by C$_1$-C$_4$-alkyl, C$_1$-C$_4$-alkoxy, hydroxyl, C$_1$-C$_4$-alkylamino, di-C$_1$-C$_4$-alkylamino, halogen and/or trifluoromethyl mono-, di- or trisubstituted naphthyl-C$_1$-C$_4$-alkoxy, each of which is unsubstituted or mono-, di- or trisubstituted by C$_1$-C$_4$-alkyl, C$_1$-C$_4$-alkoxy, hydroxyl, C$_1$-C$_4$-alkylamino, di-C$_1$-C$_4$-alkylamino, halogen and/or trifluoromethyl, polyhalo-C$_1$-C$_4$-alkoxy, optionally partially hydrogenated pyridyl- or N-oxidopyridyl-C$_1$-C$_4$-alkoxy, thiazolyl-C$_1$-C$_4$-alkoxy, optionally N-oxidized morpholino-C$_1$-C$_4$-alkoxy, thiazolylthio-C$_1$-C$_4$-alkoxy, thiazolinylthio-C$_1$-C$_4$-alkoxy, imidazolylthio-C$_1$-C$_4$-alkoxy, optionally N-oxidized pyridylthio-C$_1$-

$C_4$-alkoxy, pyrimidinylthio-$C_1$-$C_4$-alkoxy, $C_1$-$C_8$-alkanesulphonylamino-$C_1$-$C_4$-alkoxy, trifluoro-$C_1$-$C_8$-alkanesulphonyl-$C_1$-$C_4$-alkoxy, pyrrolidino-$C_1$-$C_4$-alkoxy, piperidino-$C_1$-$C_4$-alkoxy, cyano-$C_1$-$C_4$-alkoxy, carboxy-$C_1$-$C_4$-alkoxy, $C_1$-$C_4$-alkoxycarbonyl-$C_1$-$C_4$-alkoxy, carbamoyl-$C_1$-$C_4$-alkoxy, N—$C_1$-$C_8$-alkylcarbamoyl-$C_1$-$C_4$-alkoxy, N-mono- or N,N-di-$C_1$-$C_4$-alkylcarbamoyl-$C_1$-$C_4$-alkoxy, carboxy-$C_1$-$C_4$-alkyl, $C_1$-$C_4$-alkoxycarbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, carboxy-$C_1$-$C_4$-alkoxy, $C_1$-$C_4$-alkoxycarbonyl-$C_1$-$C_4$-alkoxy, carbamoyl-$C_1$-$C_8$-alkoxy, $C_1$-C and its pharmaceutically acceptable salt.

2. Compound according to claim 1, in which $R_1$ is aryl which is optionally mono- or polysubstituted by $C_1$-$C_8$-alkyl, cyano, hydroxyl, amino, $C_1$-$C_6$-alkylamino, N,N-di-$C_1$-$C_6$-alkylamino, $C_2$-$C_6$-alkenyl, $C_2$-$C_6$-alkynyl, $C_0$-$C_6$-alkylcarbonylamino, $C_1$-$C_6$-alkoxycarbonylamino, halogen, trifluoromethyl, $C_1$-$C_8$-alkoxy, optionally N-mono- or N,N-di-$C_1$-$C_8$-alkylated carbamoyl, optionally esterified carboxyl, aryl or heterocyclyl.

3. Compound according to claim 1, in which $R_1$ is an aryl substituted by $C_1$-$C_6$-alkylenedioxy.

4. Compound according to claim 1 of the formula

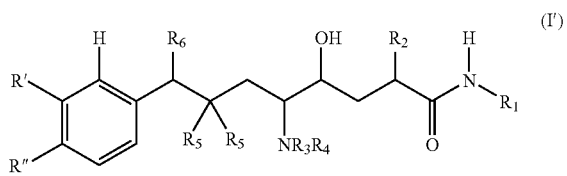

(I')

in which $R_1$, $R_2$, $R_3$, $R_4$, $R_5$ and $R_6$ are each as defined for the compound of the formula (I) and R' and R" are each independently as defined for R for the compound of the formula (I).

5. Compound according to of claim 1 of the formula

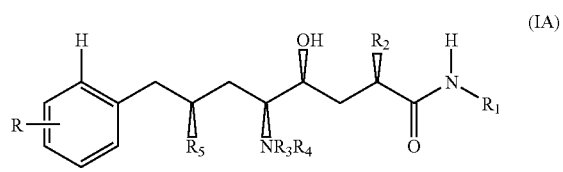

(IA)

in which R, $R_1$, $R_2$, $R_3$, $R_4$ and $R_5$ are each as defined for the compound of the formula (I).

6. Compound according to claim 1, in which
R are each independently 1-4 radicals selected from;
hydrogen, halogen, $C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy and $C_1$-$C_4$-alkoxy-$C_1$-$C_4$-alkoxy.

7. Compound according to claim 1, in which
$R_1$ is optionally substituted aryl,
$R_2$ is $C_1$-$C_8$-alkyl;
$R_3$ is hydrogen;
$R_4$ is hydrogen;
$R_5$ are each independently hydrogen or $C_1$-$C_8$-alkyl;
$R_6$ is hydrogen;
R are each independently 1-4 radicals selected from;
hydrogen, halogen, $C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy and $C_1$-$C_4$-alkoxy-$C_1$-$C_4$-alkoxy.

8. Pharmaceutical preparation comprising a compound of the general formula (I) according to claim 1, and also customary excipients.

9. Pharmaceutical combination in the form of a preparation or of a kit composed of individual components, consisting a) of a compound of the general formula (I) according to claim 1 and b) at least one drug form whose active ingredient has cardiovascular action.

* * * * *